United States Patent [19]

Cosman

[11] Patent Number: 4,787,886

[45] Date of Patent: Nov. 29, 1988

[54] PRESSURE SENSOR CONTROLLED VALVE

[76] Inventor: Eric R. Cosman, 872 Concord Ave., Belmont, Mass. 02178

[21] Appl. No.: 170,064

[22] Filed: Mar. 14, 1988

Related U.S. Application Data

[63] Continuation of Ser. No. 011,384, Feb. 5, 1987, abandoned, which is a continuation of Ser. No. 848,325, Apr. 2, 1986, abandoned, which is a continuation of Ser. No. 563,404, Dec. 25, 1983, abandoned.

[51] Int. Cl.$^4$ ............................................. A61M 27/00
[52] U.S. Cl. ........................................................ 604/9
[58] Field of Search ............................ 604/9, 10, 247; 137/510

[56] References Cited

U.S. PATENT DOCUMENTS

| | | | |
|---|---|---|---|
| 3,762,681 | 10/1973 | McKinney et al. | 137/510 |
| 3,769,982 | 11/1973 | Schulte | 604/10 |
| 3,886,948 | 6/1975 | Hakim | 604/9 |
| 3,901,245 | 8/1975 | Spitz et al. | 604/10 |
| 3,999,553 | 12/1976 | Spitz et al. | 137/510 |
| 4,464,168 | 8/1984 | Redmond et al. | 604/9 |

*Primary Examiner*—Stephen C. Pellegrino
*Attorney, Agent, or Firm*—Richard J. Birch

[57] ABSTRACT

The sensor-valve disclosed herein is an element in a fluid shunting system such as used in hydrocephalus and controls the flow of fluid in the shunt system according to the difference in pressure at some point inside the valve and the pressure in a bodily region outside and near to the valve. This is accomplished by means of a flexible diaphragm portion of the valve which communicates with the shunt fluid pressure on one side and the bodily region pressure on the other, the pressure difference causing the diaphragm to move and thus change the degree of opening of the valve fluid passage aperture. This would, for example, enable maintaining the difference between ventricular fluid pressure and pressure at the brain's surface at some desired valve in the situation of an implanted hydrocephalus shunt valve system.

10 Claims, 4 Drawing Sheets

PRESSURE SENSOR CONTROLLED VALVE

This is a continuation of co-pending application Ser. No. 011,384 filed on Feb. 5, 1987 now abandoned, which is a continuation of Ser. No. 848,325, filed on Apr. 2, 1986, now abandoned, which is a continuation of Ser. No. 563,404, filed Dec. 20, 1983, now abandoned.

BACKGROUND OF THE INVENTION

The present invention relates to a valve actuated shunt, drain, or infusion system for fluids in the living body for which the control of the fluid flow in the system is determined by the difference between the pressure of the fluid and the pressure in a bodily region external to the shunt tubing. As a specific example, this is applied to a hydrocephalus shunt valve system in which the differential pressure control is between the ventricular fluid pressure and the pressure in the surrounding brain or the pressure which is at the surface of the brain.

Usually shunt valves for treating hydrocephalus involve an in-line serial valve which allows a predetermined flow rate as a function of the difference between ventricular and venous pressure. This is simply done by inserting in-line with the shunt tubing a valve with a certain pressure-flow characteristic between its inlet and outflow tubes. An alternative servo-valve scheme has been proposed by Hakim, U.S. Pat. Nos. 4,106,510, 3,886,948, and 3,924,635, which seeks to regulate the pressure-flow characteristic of such an in-line valve system as a function of the difference between the sub-dural stress on the brain, and the venous pressure. The basis for the Hakim designs is the hypothesis that there is a pressure gradient across the brain, and that to treat hydrocephalus one should maintain the sub-dural stress at zero relative to the venous pressure.

The present invention involves a different means of regulation of the fluid flow in such a fluid shunt system. An illustration of the invention would be a valve in a shunt system which is opened, or perhaps closed, by the relative difference between the fluid pressure in the system at the source side of the flow at the location of the valve and the pressure in some bodily region different from either the fluid source or fluid sink region, i.e. input and outflow regions, respectively. A specific example is used as an illustration involving a hydrocephalus shunt system in which an indwelling valve is opened when the source fluid pressure in the ventricles of the brain become larger, by some prescribed amount, than the pressure at the surface of the brain. This could then maintain, for example, the difference between the ventricular fluid pressure and the pressure at the surface of the brain to be zero or some prescribed value. Thus, such a design differs in concept and objectives from either previous standard shunt designs or the Hakim servo-valve design. We shall often refer to the present invention as a sensor-valve.

DESCRIPTION OF THE INVENTION

Figure 1:
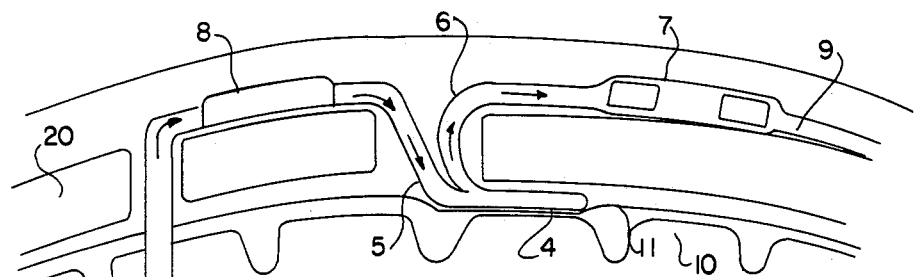
FIG. 1 shows a ventricular shunt system with an indwelling diaphragm references valve.

Referring to FIG. 1, the fluid 1 from the ventricles 2 flows through catheter 3 into a sensor-valve 4, by inlet tube 5. Fluid exits 4 by in-let tube 6 and may flow on through a standard type shunt valve 7, in-line with the system. A tentative pressure sensor 8 may also be present in the system. Distal tube 9 can carry fluid off to some final point, for instance the heart or peritoneum. Sensor-valve 4 measures pressure at the surface of the brain 10, for instance by lying against the dura membrane 11 or subarachnoid space, arachnoid, or brain surface. Valve 7 is usually designed to provide only one-way flow of fluid from the ventricles to the region that tubing 9 carries the fluid.

Figure 2:
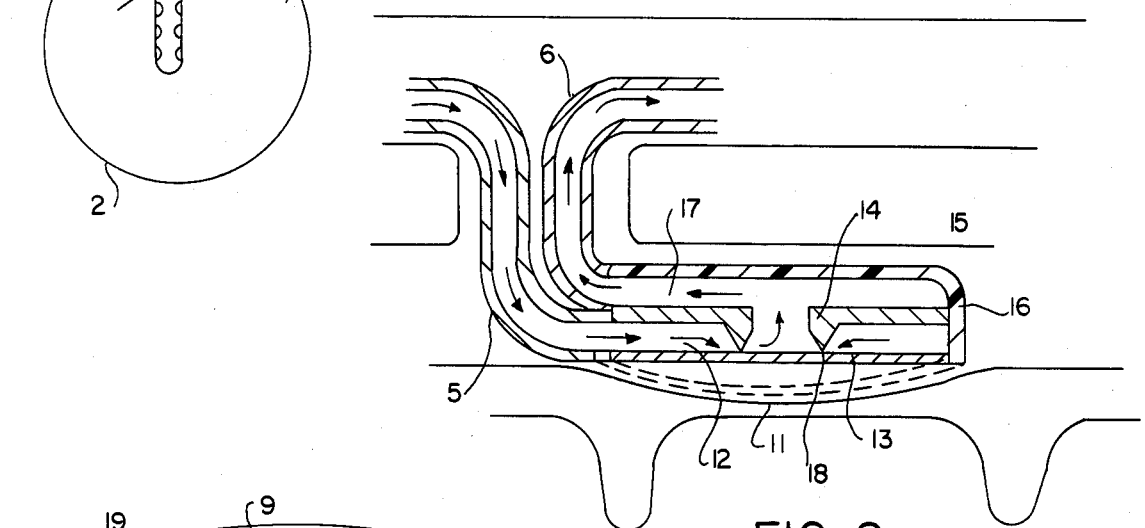
FIG. 2 shows a sectional view of the diaphragm referenced valve used in FIG. 1.

FIG. 2 is a sectional view of the sensor-valve 4 of FIG. 1. Inlet tube 5 carries fluid to chamber 12 which has a one side a diaphragm 13 that moves outward (dashed line) when the pressure in 12 increases above the pressure against 13 from the adjacent tissue 11, which could also be subarachnoid fluid pressure if tissue 11 were cut away at surgery, or brain pressure if 13 lies against or in the brain. When diaphragm 13 moves outward, it allows the fluid to flow through hole 14 and on to exit tube 6. Partition 15 may be made of hard material and body 16 acts as a closure for 13 and 16. Second chamber 17 may simply be a continuous extension of exit tube 6. Diaphragm 13 may have a predetermined tension against its stop elements 18, so that it allows fluid to flow if the pressure in 12 exceeds that just outside 13 by some predetermined amount. For instance, it may open if internal inlet pressure in 12 just equals or exceeds the pressure of the brain pressing on 13; or there may be a positive or negative off-set pressure, depending on what pressure differential is desired between ventricular pressure and surface brain pressure. Note, too, that the roles of inlet and outlet tubes may be reversed, i.e. tube 6 could have been attached to the source or ventricular tube 3, and tube 5 connected to the valve 7 and distal tube 9. This would apply if one wanted to have the sensor-valve action depend on the difference between pressure in the outlet tube and pressure on the outside of diaphragm 13. One can think of sensor-valve 4 as being a flexible portion of the tubing or fluid carrier itself such that the flow or lack of flow depends on the pressure difference immediately inside and outside of the flexible portion. Diaphragm 13 is merely a specific means of implementing the flexible portion.

Figure 3:
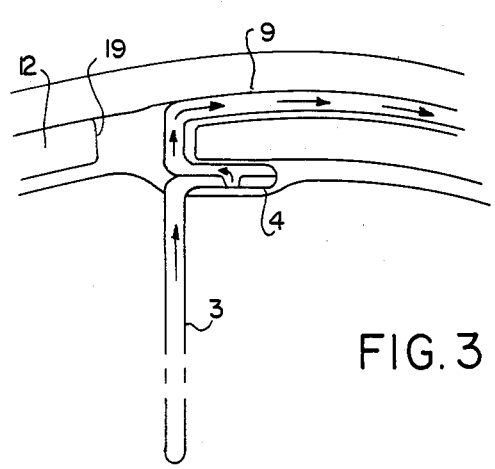
FIG. 3 shows another configuration of the device of FIG. 1.

FIG. 3 shows another arrangement in which the ventricular catheter and sensor-valve 4 are more integrally constructed so that they are implanted through the same hole 19 in the skull 20.

Figure 4:
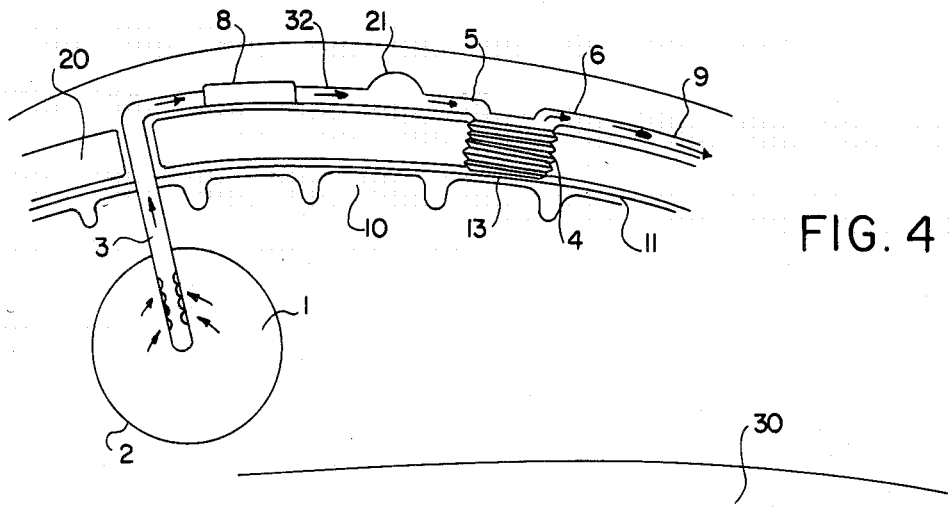
FIG. 4 shows a shunt system with a serial pressure sensor and burr hole placed diaphragm valve actuator.

FIG. 4 shows a varient of FIG. 1 in which the valve sensor 4 is more of a cylindrical element that inserts or screws into a burr hole in the skull 20 such that its lower surface diaphragm 13 senses the tissue or fluid pressure just outside it. Reservoir 21 is in-line with the inlet tubing, and may be a flexible rubber dome for pumping or injecting.

Figure 5:
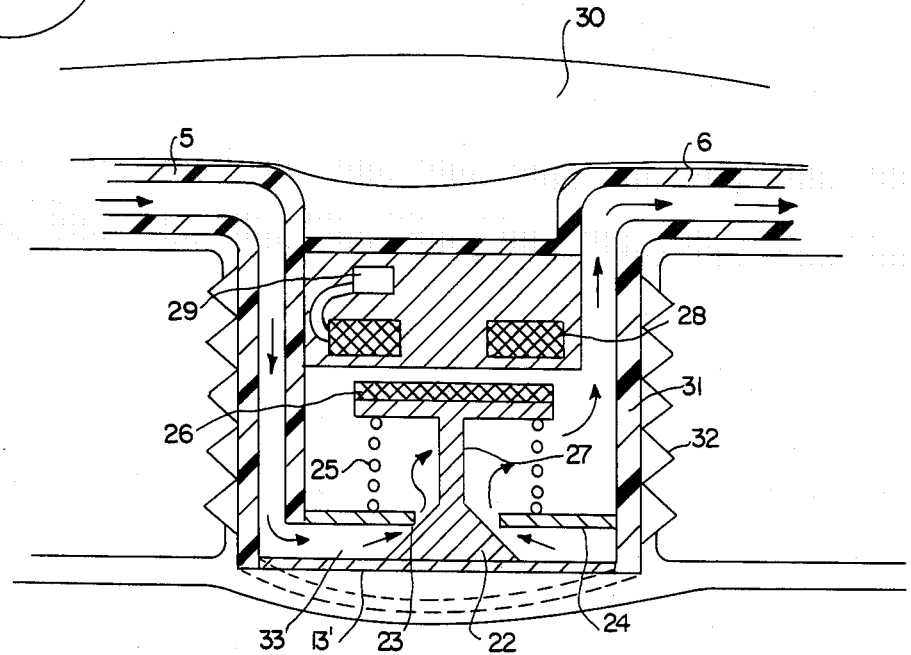
FIG. 5 shows a sectional detail view of the actuator of FIG. 4.

FIG. 5 shows a section view embodiment of valve 4 in FIG. 4. As pressure in tube 5 exceeds pressure outside 13', 13 bulges and element 22 moves away from aperture 23 in plate 24 to allow fluid to flow through the valve to tube 6. A spring 25 may put tension on 13' plus 22 to supply offset pressure or to enable a desired pressure-flow characteristic. Also shown is a telemetric circuit which allows external equipment to sense the movement of 13' and thus sense the flow or pressure difference. Element 26 may be a magnetic or conductive material which is connected to 22 and 13' by rod 27 so it moves with them. Coil 28 and capacitor 29 make an L-C circuit, the frequency of which changes as 26 displaces relative to them. The change can be detected by equipment outside the body skin 30, so that one can detect the movement of 13'. The external shell 31 may have threads 32 to screw into the skull hole. Note that having reservoir 21 in the system enables one to pull diaphragm 13' up against its closed position to check in-vivo the zero frequency of the circuit, that is its calibration frequency when the diaphragm 13' is in a position so that 22 closes or is against aperture 23. One merely depresses the reservoir by finger pressure, occludes the tubing 32 proximal to 21, and releases the reservoir. This puts a large negative pressure in region 33 of FIG. 5, pulling 13' upward, thereby closing opening 23 with element 22.

Figure 6:
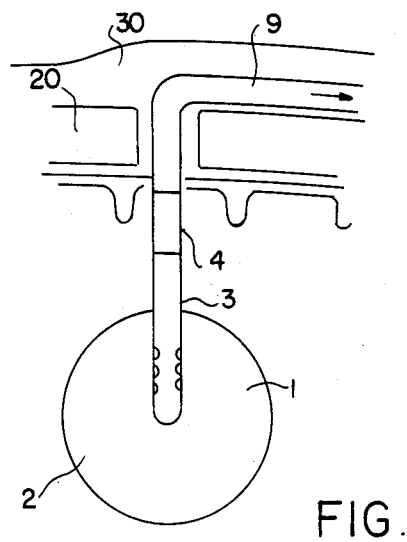
FIG. 6 shows a more in-line, compact version of FIG. 1 components.
Figure 7:
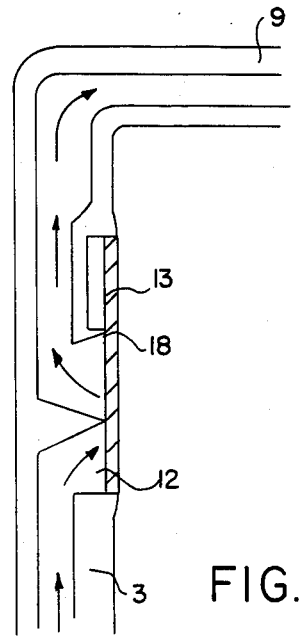
FIG. 7 shows details of the valve unit of the device in FIG. 6, in sectional view.

FIG. 6 and FIG. 7 show a variation of the sensor-valve with the sensor 4 incorporated in-line with the ventricular catheter 3 so that its diaphragm 13 senses the pressure within the brain tissue by direct contact with the tissue. FIG. 7 shows a sectional view of the sensor 4 of FIG. 6. Here diaphragm 13 may be a flexible portion of the wall of the tubing or a thinned down extension of the tube 3 itself. It works in the same way as described for FIG. 2.

Figure 8:
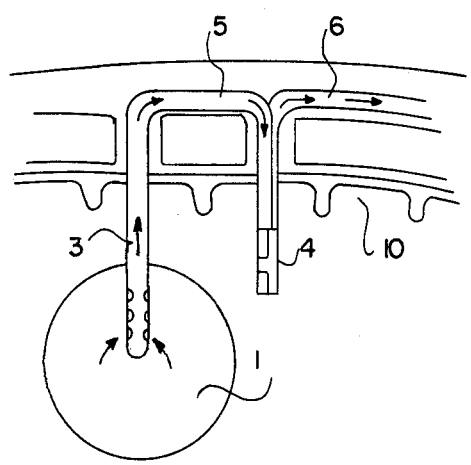
FIG. 8 shows a version of the FIG. 1 design which references the valve action to the internal pressure of the brain material itself.

FIG. 8 is another variation, where the sensor valve can be inserted into the tissue, in this case brain 10, the pressure of which is to be sensed. Sensor 4 may be a cylindrical or tubular shape such that it is easily pushed into tissue for this purpose.

Figure 9:
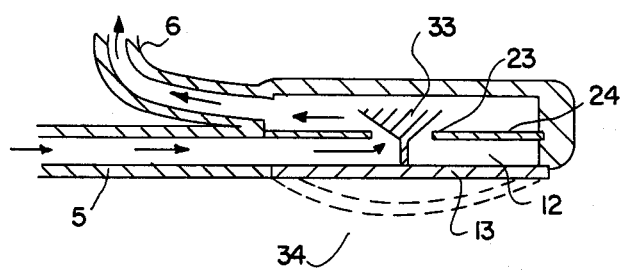
FIG. 9 shows another version of the device of FIG. 2 in which the valve opening characteristics depend on opposite roles of the internal and external pressures on the diaphragm as those of FIG. 2.

FIG. 9 illustrates another embodiment of the invention similar to that of FIG. 2 but where if pressure in chamber 12, on the inside of the diaphragm 13, is greater than the pressure in region 34, outside 13, then the bulge of 13 outward will tend to draw element 33 downward against hole 23 in plate 24 so as to close the valve. Thus, this sensor-valve works to reduce flow for pressure changes which tend to increase flow in the example of the FIG. 2. It could be that element 33, which is attached to 13, is designed to close off aperture 23 for equal pressures across 13. Then only when pressures inside chamber 12, i.e. in the fluid carried by tube 5, become negative relative to pressures outside 13, i.e. in region 34, will the valve open allowing fluid to flow. Flow is shown in FIGS. 9, 5, and 2 as going from tube 5 to 6, but clearly depending on the pressure differences across plates 24 or 15, i.e. in tubes 5 and 6, the flow may go oppositely when the valve opens.

Figure 10:
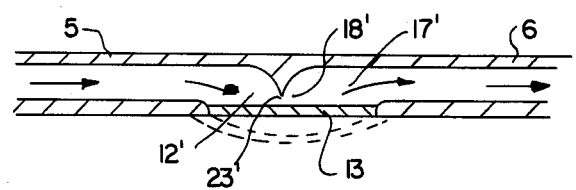
FIG. 10 shows another embodiment of the invention where the valve is almost completely integrated into the inlet tube and outlet tube.

FIG. 10 shows another geometry of the invention design where the valve is almost completely integrated into the inlet tube 5 and outlet tube 6. Here diaphragm or flexible wall portion 13 of the valve could merely be a thinned-down portion of the walls of the tubes 5 and 6 and the aperture consists merely of the lumen or opening in the tubes, perhaps with a means 18' which conveniently closes off the aperture 23' when 13' is against 18'. Chambers 12' and 17' are merely the regions on each side of the aperture region 23'. Aperture region 23' opens up when 13 bulges outward (dashed curve). Thus the concept of the formal housing 16 and aperture plate 15 and chambers 12 and 17 as illustrated in FIG. 2 can be extrapolated to this simplified construction of FIG. 10 where they are all integrated into a unit design and they all become a part of the tubing elements and a flexible wall portion ovf the tube structures or fluid carriers to perform the pressure-sensor valve function of this invention. Even the element 18' may not be necessary if one considers merely a unitized fluid carrier, equivalent to tubes 5 plus 6, with a thin flexible wall portion which closes off the lumen of the fluid carrier when pressure inside is less than the pressure outside the flexible portion, and opens up the lumen when the pressure inside exceeds the pressure outside, so that the flexible wall bulges outward.

Having described in detail various embodiments of my invention, it will now become apparent to those skilled in the art that many modifications can be made therein without departing from the scope of the invention as defined in the following claims. For instance, many different versions of the flexible wall portion or diaphragm are possible as well as the apertures, tubes, geometrics of the attached shunt, arrangement in the shunt, placement of the flexible portions in the body, etc.

What I claim and desire to secure by Letters Patent of the United States are:

1. A fluid pressure-sensor valve adapted to be implanted in the living body as part of a fluid shunting system comprising:
(a) a housing which encloses a first chamber and a second chamber;
(b) a first tube means which is in fluid communication with said first chamber;
(c) a second tube means which is in fluid communication with said second chamber, said first and said second tube means connected in said fluid shunt system so as to transport a bodily fluid that is within said shunt system;
(d) aperture means located within said housing and between said first and second chambers having an aperture designed to allow fluid to pass through it between said first and second chambers;
(e) a flexible portion of the walls of said enclosure which communicates on its inside surface with the fluid pressure in said first chamber and on its outside surface with pressure in a bodily region outside said housing, said flexible portion being in mechanical communication with the pressure in the bodily region located outside of the housing and, said flexible portion being designed to distort in shape according to the difference in pressure of the fluid in said first chamber and the pressure in the bodily region located outside of said housing and in pressure communication with said flexible wall portion, said flexible portion being so positioned and cooperatively designed relative to said aperture means that the flexible portion closes said aperture means when the pressures on both sides of the flexible portion are equal and that said flexible portion will distort with changes in the difference in pressure in said first chamber relative to the pressure in said bodily region thereby changing the degree of opening of said aperture to fluid flow through said aperture; whereby said pressure sensor valve is implanted in the living body as part of a shunt system to allow flow of a bodily fluid through said shunt system and through said aperture of said pressure-sensor valve, the flow of said bodily fluid through said aperture between said first and second chambers will be dependent on said difference in pressures in said first chamber and said bodily region outside said housing and adjacent to said flexible means, and the flow of said bodily fluid will be changed by a deformation of said flexible portion relative to said housing.

2. The pressure sensor valve of claim 1 wherein said flexible portion of said housing wall is so cooperatively positioned and designed relative to said aperture that said flexible portion closes said aperture for valves of the pressure in chamber one being less than the pressure in said bodily region outside of said flexible portion by a predetermined amount, and said flexible portion bulges outward when the pressure in said chamber exceeds the pressure in said bodily region by said predetermined amount thereby opening said aperture for flow of fluid through said aperture.

3. The pressure-sensor valve of claim 2 wherein said predetermined amount is zero so that said aperture is closed when said pressure in chamber one is less than the pressure in said bodily region outside of and adjacent to said flexible portion, and said aperture opens when said pressure in chamber one just exceeds the pressure in said bodily region.

4. The pressure-sensor valve of claim 2 which is adapted in-series with a fluid shunt valve system which has a one-way flow characteristic so as to permit flow only in the direction from chamber one to chamber two.

5. The shunt system of claim 4 which is adapted to treatment of hydrocephalus of the brain wherein said first tube means carries fluid from the ventricles of the brain and said second tube means carries fluid away to other portions of the body, and wherein said flexible portion is adapted to be placed during implantation so as to communicate on its outside surface with pressure near the surface of the brain, whereby said shunt system allows fluid to pass through said pressure-sensor valve and thus through said shunt system only if the pressure in the fluid from the ventricles at the location of said chamber one exceeds the pressure in the region of the brain which is in pressure communication with said flexible portion.

6. A fluid pressure-sensor valve adapted to be implanted in the living body as part of a fluid shunting system comprising:
 (a) a housing with an aperture therethrough;
 (b) fluid inlet and fluid outlet means connected to said housing which enable said housing to be connected to a fluid carrying shunting system when implanted in the living body and such that fluid in said shunting system can pass through said inlet means, and onward through said aperture, and on through said outlet means;
 (c) a flexible portion of the walls of said housing having an inside surface and an outside surface, said inside surface being in pressure communication with the fluid that is on the inlet means side of said aperture, and said outside surface being in mechanical pressure communication with a bodily region outside of and adjacent to said flexible portion when implanted in the living body; said flexible wall portion and said aperture being so designed and cooperatively positioned that the flexible portion closes said aperture means when the pressures on both sides of the flexible portion are equal and that said flexible wall portion will distort with changes in the difference of said pressure on said inside surface relative to said pressure on said outside surface, thereby changing the aperture opening of said aperture and thus changing the rate of flow of fluid that passes through said aperture as a function of fluid pressures in said inlet and outlet means.

7. The device of claim 6 wherein said aperture is closed when said pressure on said inside surface is less than said pressure on said outside surface, and open when said pressure on said inside surface exceeds that on said outside surface.

8. The device of claim 6 wherein said aperture is closed when said pressure on said inside surface is greater than said pressure on said outside surface, and open when said pressure on said inside surface is less than that on said outside surface.

9. The device of claim 6 wherein said aperture is opened when the difference between said pressure on said inside surface and said pressure on said outside surface exceeds a predetermined value.

10. The device of claim 6 which is so adapted that, when implanted within the living body such that said inlet means is in fluid communication with the ventricles of the brain, said housing can be implanted in such a position that said outside surface of said flexible portion can be placed in pressure communication with the outer portion of the brain, whereby said pressure-sensor valve acts to regulate the flow of fluid from the ventricles of the brain in accordance with the difference between said pressures on the inside and the outside of said flexible means which is related to the difference between the pressure of the fluid in the ventricles and the pressure in the brain which communicates with said surface of said flexible portion.

* * * * *